(12) United States Patent
Frazee et al.

(10) Patent No.: US 10,106,653 B2
(45) Date of Patent: Oct. 23, 2018

(54) CONTINUOUS HIGH SHEAR REACTOR MELT PROCESSING METHODS TO SYNTHESIZE HETEROCYCLIC MONOMER AND PREPOLYMER ALLOYS AND COMPOSITIONS THEREOF

(71) Applicants: Andrew S. Frazee, Hattiesburg, MS (US); Jeffrey S. Wiggins, Petal, MS (US)

(72) Inventors: Andrew S. Frazee, Hattiesburg, MS (US); Jeffrey S. Wiggins, Petal, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 0 days.

(21) Appl. No.: 15/368,533

(22) Filed: Dec. 2, 2016

(65) Prior Publication Data
US 2017/0166698 A1   Jun. 15, 2017

Related U.S. Application Data

(60) Provisional application No. 62/261,970, filed on Dec. 2, 2015.

(51) Int. Cl.
*C08G 73/10* (2006.01)
*C07D 265/16* (2006.01)

(52) U.S. Cl.
CPC ....... *C08G 73/1092* (2013.01); *C07D 265/16* (2013.01)

(58) Field of Classification Search
CPC .................................................. C08G 73/92
USPC ................................................... 544/90
See application file for complete search history.

(56) References Cited

U.S. PATENT DOCUMENTS 5,543,516 A * 8/1996 Ishida .................. C07D 265/16
544/69

* cited by examiner

*Primary Examiner* — Kahsay Habte
(74) *Attorney, Agent, or Firm* — Lawrence Arthur Schemmel

(57) ABSTRACT

The invention provides novel methods of synthesizing new monofunctional and/or multifunctional heterocyclic monomer and prepolymer alloys via a continuous solvent-free, or alternatively in-solvent, one-step high shear reactor methodology designed to eliminate the need for post-processing purification and react monomer to predictable conversions, as well as the synthesis of related compositions. Additionally, the invention allows the dispersion of reinforcements and additives while synthesizing heterocyclic monomers and formulating heterocyclic prepolymer alloys.

15 Claims, 6 Drawing Sheets

Example A  Example B

CONTINUOUS HIGH SHEAR REACTOR MELT PROCESSING METHODS TO SYNTHESIZE HETEROCYCLIC MONOMER AND PREPOLYMER ALLOYS AND COMPOSITIONS THEREOF

CROSS-REFERENCE TO RELATED APPLICATION

This application claims priority from U.S. Provisional Patent Application Ser. No. 62/261,970 filed Dec. 2, 2015. The entirety of the provisional application is incorporated herein by reference.

FIELD OF THE INVENTION

This invention relates to the field of thermoset composite matrix production and processing and, more specifically, to novel methods of synthesizing monofunctional and/or multifunctional heterocyclic monomer and prepolymer alloys and reacting monomers to prepolymers of predictable conversion via a continuous, solvent-free, or alternatively in-solvent, one-step methodology designed to eliminate the need for post-processing purification and react monomer to predictable prepolymer conversions and to the synthesis of related compositions.

SUMMARY OF THE INVENTION

The present invention provides a novel solvent-free, or alternatively in-solvent, continuous high shear reactor adept to synthesize heterocyclic monomer and prepolymer alloys and react to predictable conversions in a one-step method. Specifically, the invention allows the synthesis of the monofunctional heterocyclic monomers without the need for purification and reduced isomer content. Furthermore, the invention discloses the ability to synthesize heterocyclic prepolymers comprised of monofunctional and/or multifunctional heterocyclic species that were reacted to prepolymer using the described one-step high shear continuous reactor methodology without the need for post-processing purification.

The invention also provides the ability to disperse reinforcements and additives while synthesizing heterocyclic monomers and formulating heterocyclic monomer alloys created by the methods and system of the invention. The invention provides for methods to form heterocyclic prepolymer alloys using the novel compositions of the invention, including for example the monofunctional benzoxazine monomer, multifunctional benzoxazine monomer, monofunctional maleimide monomer, and/or the multifunctional bismaleimide monomer compositions.

With the foregoing and other objects, features, and advantages of the present invention that will become apparent, the nature of the invention may be more clearly understood by the following detailed description of the preferred embodiments of the invention and by the appended claims.

BACKGROUND OF THE INVENTION

Characteristic traits of heterocyclic chemistries, such as polybenzoxazines and polybismaleimides, are considered to couple the thermal properties and fire retardance of phenolic matrices with the modular molecular design of epoxies. This combination renders benzoxazines an attractive matrix chemistry for high performance composite applications. Furthermore, benzoxazines possess the ability to form an alloy with other matrix chemistries affording tailorable physical properties and solventless processing, which provide the added benefit of environmentally-favorable manufacturing.

Compared to the current industrial batch reactor methods used to produce benzoxazine monomer and prepolymer, the novel reactor design of the present invention provides a cost-effective and environmentally-favorable technique that reduces reaction time, reduces the amount of isomer formation, and eliminates the need for any post-reaction purification steps. The ability to produce these heterogeneous syntheses in a continuous reactor via the invention also avoids batch-to-batch variations, which plagues batch reactor methods. Additionally, this novel continuous high shear reactor methodology is a viable technique for up-scaled production of such heterocyclic monomer and prepolymer systems. Herein, the continuous high shear reactor that is utilized has the ability to feed reactants independently, for staged reaction cascade, or for a preblended batch approach. Moreover, the novel methods provide the ability to control the temperature, time, and shear in the processing section. The control and feed system features of the invention enable the ability to produce high volumes of heterocyclic monomer alloys and prepolymer alloys with predictable prepolymer conversion and reduced isomer content and to eliminate the need for post-processing purification via a cost-effective and environmentally-favorable one-step method.

Heterocyclic chemistries such as benzoxazines have previously been synthesized in solvent-free and single-screw reactors. However, a single-step, solvent-free synthesis methodology of heterocyclic monomer (monofunctional and/or multifunctional) and prepolymer alloy production with increased reaction efficiency and elimination of post-processing purification is unreported in the current scientific and patent literature. The present invention provides such novel methodologies whereby a continuous, high shear reactor is comprised of at least one co-rotating twin-screw extruder, which is highly modular with respect to structural design, feed delivery systems, and experimental parameters, for example, but not limited to processing temperature, residence time, screw speed, and/or screw design.

The solvent-free, continuous high shear reactor methods and system of the present invention provide a cost-effective, environmentally-favorable, and scaleable method to synthesize heterocyclic monomer and prepolymer alloys. The invention alternatively can be utilized in-solvent.

Continuous Chemical Reactors

Continuous Reactive Processing:

With international attention of media and consumers focused on sustainability, "green" manufacturing is an area of technology for which global and regional governmental agencies and corporations are willing to pay a premium to reduce emissions, energy consumption, and toxic substances. Polymerization reactors and processes (i.e. batch systems) are commonly energy intensive and produce inconsistent product quality. The production of epoxies used as structural matrices in fiber reinforced aerospace materials provides a great example. In this process, a batch reactor is charged with large volumes of monomer (epoxy and amine) and tougheners (thermoplastic) to which heat is applied to advance molecular weight, forming "b-staged" epoxy prepolymers. These prepolymers are then discharged and stored in freezers to reduce continued reactions until reheated and applied as a thin film for prepreg manufacturing. The energy consumption from batch heating, sub-ambient storage, and filming results in substantial production costs. Nonetheless, elevations in direct manufacturing costs are incurred from batch-to-batch variations in material quality and opportunity costs from downtime and accumulated inventory during the sub-ambient storage.

Advancements in twin screw extrusion technology for thermoplastic compounding and continuous polymerization reactors have matured since the initial concepts proposed by Wunsche and Easton in the early 1900s. As reported in the literature by Brown & Orlando and Xanthos, process capabilities for twin screw extruders (TSE) have expanded as continuous reactors, bulk polymerization reactors, polymer grafting reactors, and polymer blend compatibilization reactors. Compared to batch reactors, the primary advantage of reaction extrusion is credited to the extruder's ability to transport a broad range of viscosities and molecular weights simultaneously. Furthermore, the absence of solvent coupled with low volume processing and high throughputs improve energy consumption affording an environmentally-favorable reactive process. TSE process designs are extremely modular offering precision feeding, mixing, controlled shear energies, excellent heat transfer, insensitivity to viscosity changes, and devolatilization.

Modular Processing Designs of Continuous Chemical Reactors:

It is well-documented that fully intermeshing co-rotating twin screw extruders provide the highest level of mixing, dispersion, and shear control, making them the primary unit for continuous chemical reactors. Intermeshing co-rotating twin screw extruders offer a multitude of screw elements providing modularity in the screw design to achieve effective material transport, mixing, and shear. Examples of typical intermeshing co-rotating modular screw elements for screw designing are various flighted conveying elements, kneading blocks (neutral, right, and left), and ZME. The most common continuous reactor screw design includes conveying elements, kneading elements, and mixing elements.

Reactor screws are designed specifically for the material and the targeted function of the process (i.e. blending, dispersing, etc.). Reactor screws are precision tolerance fit within a series of "barrel sections" that are independently temperature-controlled. Additionally, the barrel sections are interchangeable providing the flexible design of inlets to various liquid reactants, solid reactants, and catalysts, as well as vacuum ports for devolatilization along the reactor. A common processing section of a continuous chemical reactor comprises modular components including barrel sections, liquid feed, solid feed, and twin screws, for example.

The present invention discloses novel continuous high shear reactor providing a cost-effect, environmentally-favorable, and scaleable design methods to synthesize heterocyclic monomer (monofunctional and/or multifunctional) and prepolymer alloys and prepolymers with predictable conversions with increased reaction efficiency and elimination of post-processing purification. Furthermore, the high shear environment enables the simultaneous dispersion of reinforcements and additives while synthesizing the heterocyclic monomer and prepolymer alloys and prepolymers with predictable conversions.

BRIEF DESCRIPTION OF THE DRAWINGS

The drawings and Figures shown within the specification accompany the detailed description of the invention and are intended to illustrate further the invention and its advantages. The drawings and Figures, which are incorporated in and form a portion of the specification, illustrate certain preferred embodiments of the invention and, together with the entire specification, are meant to explain preferred embodiments of the present invention to those skilled in the art. Relevant FIGURES are as follows.

DETAILED DESCRIPTION OF THE INVENTION

The invention provides methods of synthesizing novel monofunctional and/or multifunctional heterocyclic monomers and the formulation of novel monomer and prepolymer alloys with predictable conversions of said monomers from base reactants via a continuous solvent-free, or alternatively in-solvent, one-step high shear reactor methodology designed to reduce the minor isomer formation and to eliminate the need for post-processing purification. Moreover, the invention provides the ability to disperse reinforcements and additives while synthesizing such heterocyclic monomers and monomer alloys created and provides for the synthesis of related compositions. All parameters presented herein including, but not limited to, temperatures, pressures, times, sizes, amounts, ratios, weights, and/or percentages, for example, represent approximate values. References to 'a' or 'an' concerning any particular item, component, material, or product is defined as at least one and could be more than one.

The present invention provides for new methods to formulate monomer and prepolymer alloys and prepolymers with predictable conversions comprised of monofunctional and/or multifunctional heterocyclic monomers, such as but not limited to benzoxazines and bismaleimides, from any known variant of the base reactants, from a batch of pre-blended or independently-fed reactants, without the need for post-processing purification in a single-step and solvent-free, or alternatively an in-solvent, design. Simultaneously, the invention also provides the ability to disperse reinforcements and/or additives while formulating said alloys.

The invention provides for methods for forming and/or synthesizing heterocyclic monomer and prepolymer alloys utilizing novel compositions, including for example the monofunctional benzoxazine monomer, multifunctional benzoxazine monomer, monofunctional maleimide monomer, and/or the multifunctional bismaleimide monomer compositions, or a combination of such compositions. The invention further provides for the ability to predictably control the prepolymer alloy formation and/or conversion by controlling specific temperatures of the reactor and by controlling process control variables including, but not limited to, screw and/or mixing speed, composition throughput, or a combination thereof.

Figure 1:
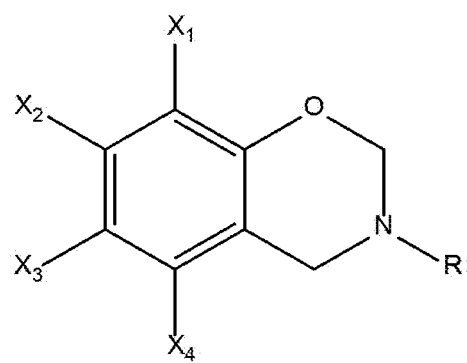
FIG. 1 depicts monofunctional benzoxazine monomer general structures of the present invention.
Figure 2:
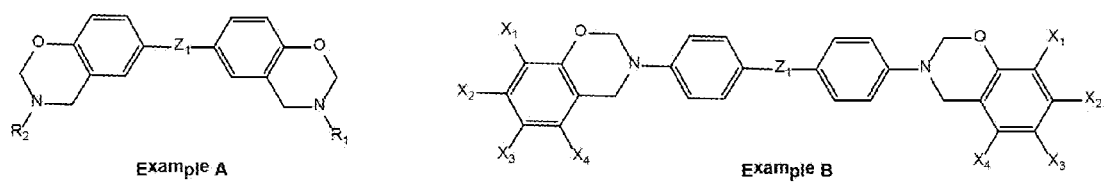
FIG. 2 depicts multifunctional benzoxazine monomer general structures of the present invention.

The invention relates to the melt synthesis of any monofunctional (FIG. 1, FIG. 3) and/or multifunctional (FIG. 2, FIG. 4) heterocyclic monomers in the application of matrices comprised of heterocyclic chemistries for high performance thermoset composites. Specifically, the invention pertains to variants of monofunctional benzoxazine monomers, as in FIG. 1, wherein substituents $X_{1-4}$ on phenol can be an electron withdrawing group, for example but not limited to F, Cl, Br, I, COH, CN, COCH$_3$, COOCH$_3$, SO$_3$H, or NO$_2$, electron donating group, for example but not limited to OCH$_3$ or CH$_3$, hydrogen (H), alkyl (C$_{1-8}$ alkyl), cycloalkyl (C$_{5-7}$ cycloalkyl), and aryl, where the aryl and cycloalkyl can be substituted with the mentioned electron withdrawing or electron donating groups. The R groups on a primary amine can be H, C$_{1-8}$ alkyl, C$_{5-7}$ cycloalkyl, and aryl. Furthermore, the cycloalkyl and aryl can be substituted with any of the mentioned X and/or R groups previously mentioned. Also, the invention pertains to families of multifunctional benzoxazine monomers, as in FIG. 2, wherein Z$_1$ can be selected from —C(O)—, —S—, —O—, S(O)—, —S(O)$_2$—, or —C(CH$_3$)$_2$— on a bis-phenol or bis-amine, for example but not limited thereto. The X groups ($X_{1-4}$) of a phenol can be, for example but not limited to, an electron withdrawing group F, Cl, Br, I, COH, CN, $COCH_3$, $COOCH_3$, $SO_3H$, or $NO_2$, electron donating group $OCH_3$ or $CH_3$, unsubstituted or hydrogen (H), alkyl ($C_{1-8}$ alkyl), cycloalkyl ($C_{5-7}$ cycloalkyl), and aryl, where the aryl and cycloalkyl can be substituted with (or contain) for example but not limited to the mentioned electron withdrawing and/or electron donating groups. Lastly, the R groups ($R_1$ and $R_2$) of a primary amine can be H, $C_{1-8}$ alkyl, $C_{5-7}$ cycloalkyl, and aryl, for example but not limited thereto. Furthermore, the cycloalkyl and aryl can be substituted with or contain any of the mentioned X and/or R groups previously mentioned, for example but not limited thereto.

Figure 3:
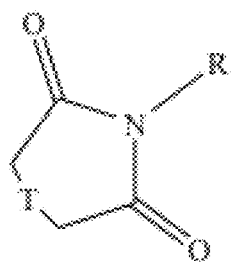
FIG. 3 depicts a monofunctional maleimide monomer general structure of the present invention.
Figure 4:
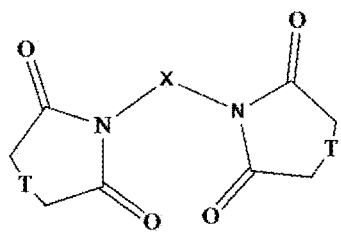
FIG. 4 depicts multifunctional bismaleimide monomer general structures of the present invention.
Figure 4:
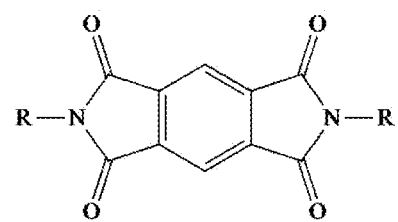

The present invention also relates to the melt synthesis of any variants of monofunctional maleimide monomers, as in FIG. 3, wherein T on the anhydride structure can be a double bond, a single bond, and/or contain additionally bonded substituents at either carbon of T an electron donating group, for example but not limited to, $OCH_3$ or $CH_3$, hydrogen (H), alkyl ($C_{1-8}$ alkyl), cycloalkyl ($C_{5-7}$ cycloalkyl), and aryl, where the aryl and cycloalkyl can be substituted with and/or contain the mentioned electron donating groups. The R groups on a primary amine can be, for example but not limited to H, $C_{1-8}$ alkyl, $C_{5-7}$ cycloalkyl, or aryl. Furthermore, the invention pertains to families of multifunctional bismaleimide monomers, as in FIG. 4, wherein X can be selected from —C(O)—, —S—, —O—, S(O)—, —S(O)$_2$—, or —C(CH$_3$)$_2$— on a bis-amine or bis-anhydride, for example but not limited thereto. The R groups on a primary amine can be, for example but not limited to H, $C_{1-8}$ alkyl, $C_{5-7}$ cycloalkyl, or aryl.

Figure 5:
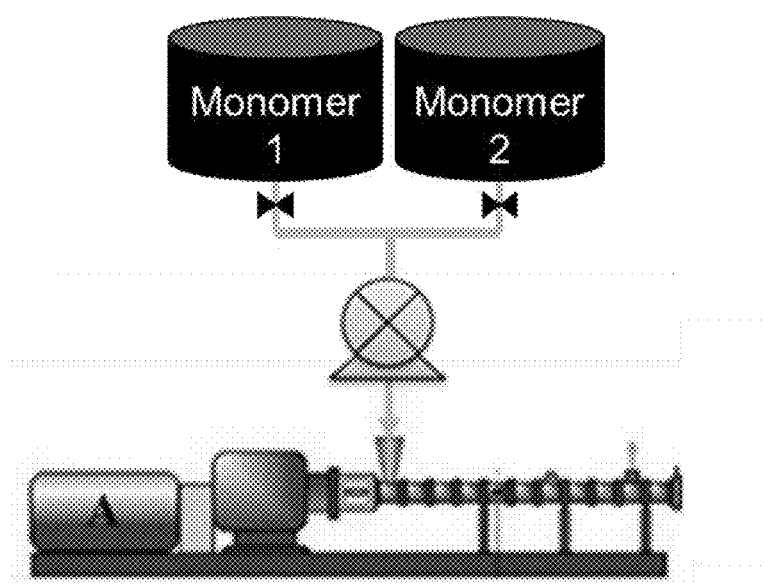
FIG. 5 depicts a schematic of the continuous high shear reactor method of the present invention.

The invention provides for the continuous high shear reactor method shown in FIG. 5, such that derivatives of the mentioned monofunctional and/or multifunctional monomer and prepolymer alloys can be formulated and reacted to predicted prepolymer conversions. The example of the process design in FIG. 5 of the invention is capable of any amount of individually-fed monomers/prepolymers, pre-blended batch monomers/prepolymers, and combinations thereof, for example. The present invention therefore discloses methodology to formulate heterocyclic monomer and prepolymer alloys and melt synthesize heterocyclic monomers and prepolymers_with predictable conversions utilizing a continuous high shear reactor set to processing temperatures of from about 140° C. to about 200° C. and residence time of from about 60 seconds to about 90 seconds for benzoxazines. The benzoxazine monomer alloys and the prepolymer alloys are comprised of monofunctional benzoxazine monomers (FIG. 1) and/or multifunctional benzoxazine monomers (FIG. 2) synthesized from any known variant(s) of base reactants herein, for example.

The monomer (Schemes A & B) and prepolymer alloys, derived from prepolymers of Schemes A & B, can be successfully synthesized in about 60-90 seconds without the need for post-processing purification. The process design in FIG. 5 is comprised of a reactor (FIGS. 5, 1) that is a co-rotating twin-screw extruder, which is highly modular accommodating for the change in reaction kinetics for each variant of the listed monofunctional and multifunctional benzoxazine monomers. FIG. 5 depicts two monomer vessels, while the invention provides for at least one monomer vessel and alternatively and typically for more than one monomer vessel. Specifically, the monomers (Scheme A), can be fed independently from each other or in any combinatorial option. Furthermore, the high shear environment afforded by the present invention enables the ability to effectively disperse any type of reinforcement and/or additive while synthesizing benzoxazine monomers. Reactive diluents can be added to the synthesis at weight ratios of from about 0 to 100 weight percent and can include, for example, monofunctional and multifunctional epoxies and curatives, or a combination thereof.

Additionally, at least one reinforcement such as carbon nanotubes, graphene, POSS, silica, carbon black, and fibers, for example, and/or at least one additive such as pigments, organic matter, dispersants, molecular sieves, and flocculants, for example, or a combination thereof, can be added to the synthesis process at weighted ratios of from about 0 to about 100 weight percent. The addition of any such reinforcement and/or additive, or combination thereof, is at a weighted ratio of from about 0 to about 100 weight percent.

Utilizing the present invention, it has been demonstrated that the reaction efficiency is increased, as compared to batch reactors and other reactors from current technologies, because the reaction time is reduced and the need for post-processing purification is eliminated.

Scheme A: Materials used and product formed using the continuous high shear reactor

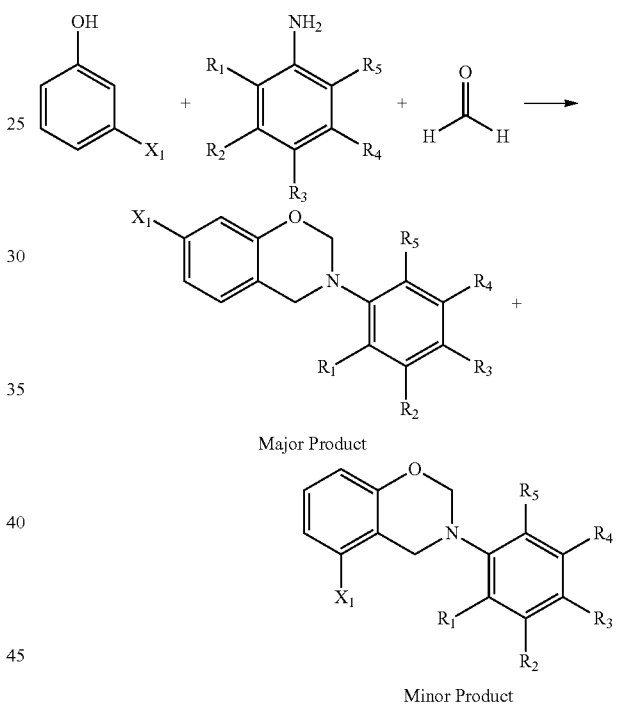

Scheme A: Materials Used and Product Formed Using the Continuous High Shear Reactor Although benzoxazine monomers and prepolymer alloys have been reportedly melt synthesized in batch reactors and single-screw extruders, there is no prior work or technology that exhibits the truly "continuous" and single-step reactor design of the present invention wherein the base reactants can be fed independently and yield high purity product about 6-40× faster than currently reported. Current technology has been unable to achieve successful monomer synthesis in about 30-60 seconds at temperatures above about 100° C. as the invention. Other technologies have been unable to and have failed to increase the reaction efficiency and efficacy, favoring the major product of a potential isomeric blend, and cannot eliminate the need for post-processing purification by synthesizing high purity product utilizing the continuous high shear reactor methods disclosed in the present invention.

There are no known reports demonstrating a continuous high-shear reactor to synthesize bismaleimides under solvent-free conditions, with reactions times less than about 90 seconds and yielding a high purity product as the invention provides. The major isomer of room temperature solid and/or liquid monofunctional and/or multifunctional benzoxazine monomers can be synthesized utilizing the methods of the present invention. Moreover, the invention provides for synthesis of about 100% benzoxazine monomer and prepolymer alloys comprised of room temperature solid and/or liquid monofunctional and/or multifunctional benzoxazine analogues, fed independently and/or from a blended batch, at ratios of from about 0 wt. % to about 100 wt. % of monofunctional to multifunctional benzoxazine monomer, and having greater than about 80% to greater than about 99% purity and eliminating the need for post-processing purification and providing the synthesis thereof in a single-step. The methodologies of the invention also provide for minimization of the formation, or even elimination, of any minor isomer.

The invention further allows for the synthesis of from about 0 to about 100 percent heterocyclic monomer alloys and prepolymer alloys comprised of room temperature liquid and/or solid monofunctional and/or multifunctional heterocyclic analogues at ratios of about 0 to about 100 percent monofunctional heterocyclic monomer to multifunctional heterocyclic monomer, respectively.

Additionally, the invention provides the ability to synthesize prepolymer alloys comprised of monofunctional and/or multifunctional heterocyclic monomer repeat units. The prepolymers can contain repeat units of any combination of the heterocyclic chemistry described. Utilizing the robust control of processing temperature (about 90-200° C.) and residence time distribution (about 60-90 seconds) afforded by the present invention for benzoxazines, the inventors were able to ring open 100% difunctional (Example 1) and monofunctional benzoxazine monomers (Scheme A) with multifunctional benzoxazine monomers (Scheme B) (Example 2) with predictable results.

Scheme B: Generalized reactions (I & II) to synthesize monofunctional and multifunctional benzoxazine monomer and prepolymer

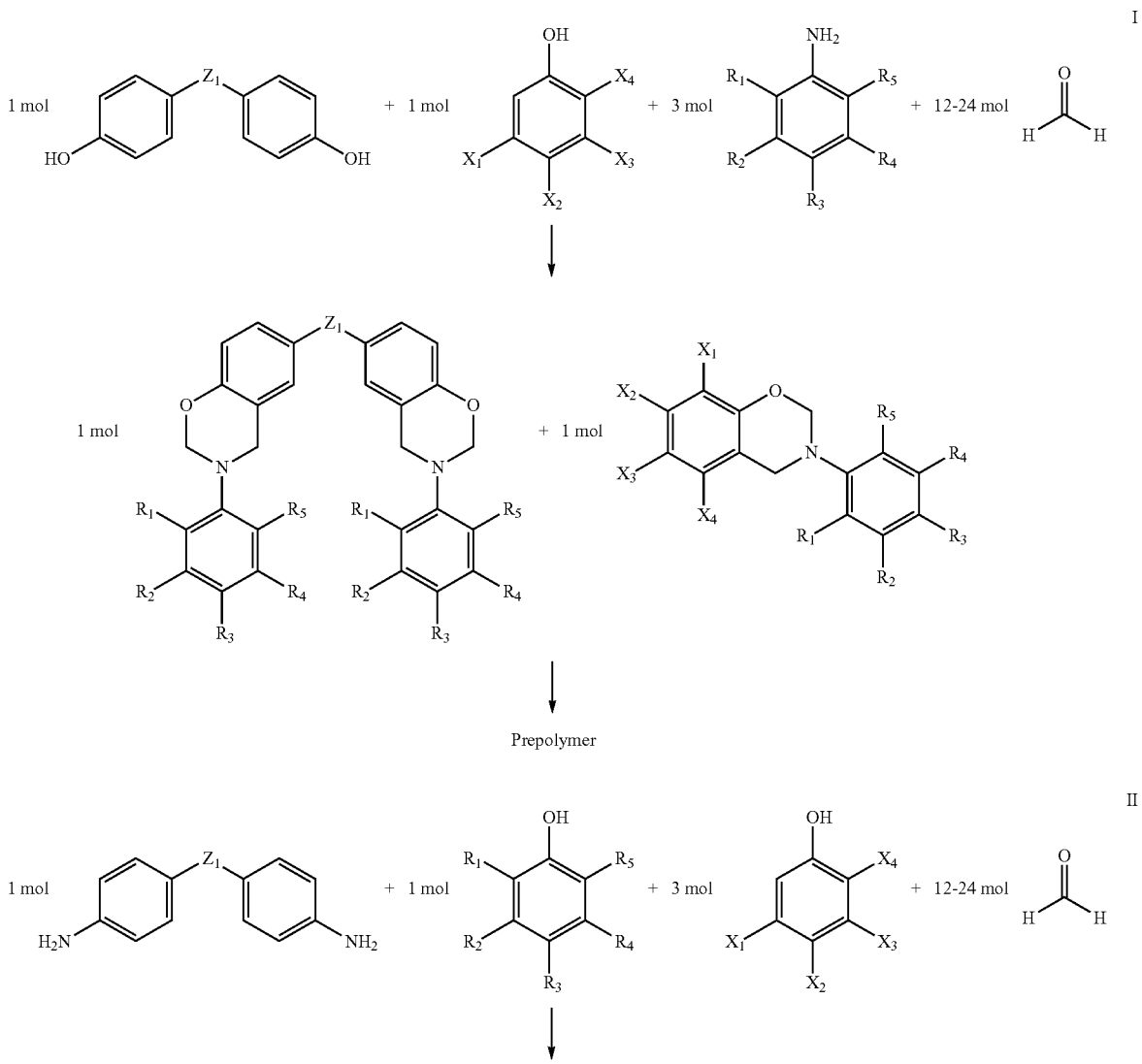

-continued

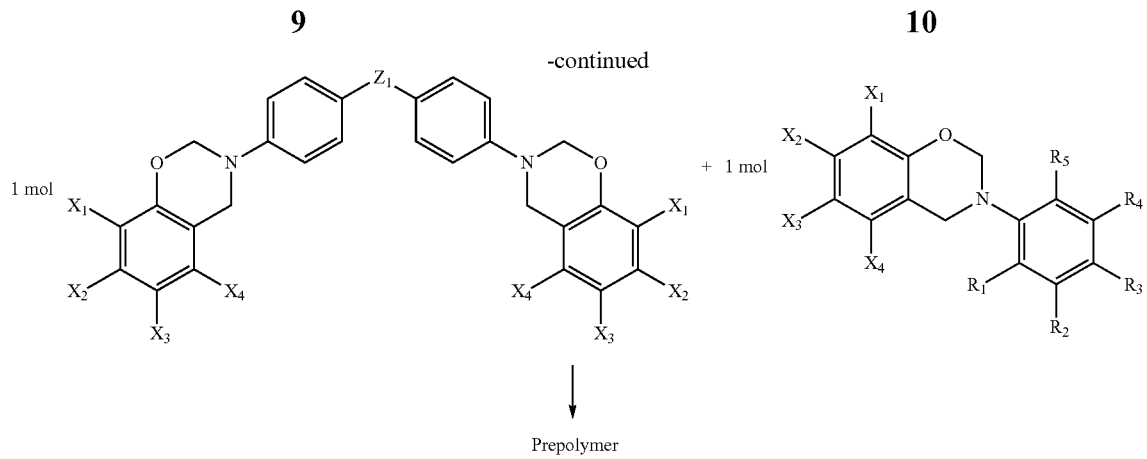

Prepolymer

Scheme B: Generalized Reactions (I & II) to Synthesize Monofunctional and Multifunctional Benzoxazine Monomer and Prepolymer Prepolymers can be comprised of any monofunctional and/or multifunctional comonomer concentration. Moreover, the high shear environment and modularity in screw design affords the ability to disperse any reinforcements and/or additives in weight percentages of from about 0-99% while synthesizing these heterocyclic monomer and prepolymer alloys.

The single-step solvent-free synthesis methods involving heterocyclic monomer (monofunctional and/or multifunctional) and prepolymer alloys and reacting monomers to prepolymers of predictable conversion of the present invention with increased reaction efficiency and elimination of post-processing purification is unreported in the current scientific and patent literature. The present invention discloses cost-effective, environmentally-favorable, and scaleable design methods for the aforementioned syntheses of heterocyclic monomer and prepolymer alloys, while also providing the ability to disperse reinforcements and additives. Such a single-step continuous reactor methodology reduces waste, batch-to-batch variations, and energy consumption, and eliminates the use of harmful solvents, although the invention may also be utilized in-solvent. Synergistically, these attributes provide a novel reactor method and market-changing opportunities for the synthesis of heterocyclic chemistries in high performance, thermoset composite industries.

In the following examples, all reactions were conducted under solvent-free conditions, while solvents could also have been used as well. Reaction parameters of reactor temperatures and process control variables such as screw and/or mixing speed(s), composition(s) throughput, or a combination thereof, for example, were predictably controlled and monitored.

Example 1 (100% BPA-Based Difunctional Benzoxazine Prepolymer Trial)

Figure 6:
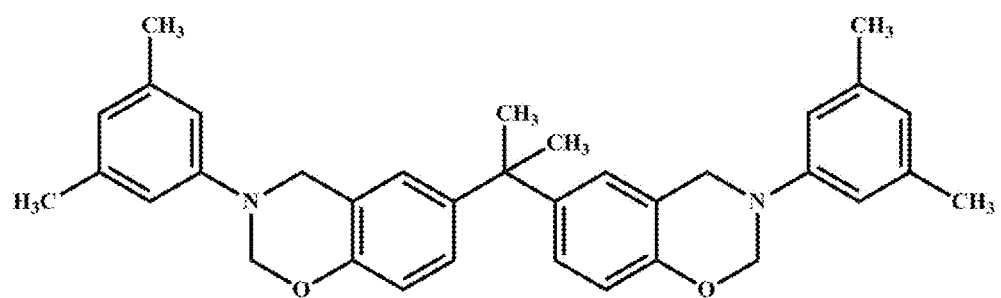
FIG. 6 depicts the chemical structure of BPA-based difunctional benzoxazine monomer (BPABOX) used to create the heterocyclic prepolymer of the present invention.

BPA-based difunctional benzoxazine monomer (BPA-BOX), the chemical structure of which is depicted in FIG. 6, was fed (unreacted) at a throughput of about 0.9 lbs/hr into zone 1 of the 16 mm PRISM reactor. Zones 1-5 were set to temperatures of from about 160° C. to about 200° C. The screw speed was set to about 300 RPM. Aliquots were collected between the aforementioned temperature range and the conversion was found to range from about 1% to about 26%.

Example 2 (70% BPA-Based Difunctional & 30% Liquid Monofunctional Benzoxazine Alloy Prepolymer Trial)

A benzoxazine monomer alloy comprised of about 70 wt. % BPABOX (unreacted) and about 30 wt. % liquid monofunctional monomer (unreacted) was synthesized and reacted at a throughput of about 0.9 lbs/hr in the 16 mm PRISM reactor. Zones 1-5 were set to from about 140° C. to about 200° C. Aliquots were collected between the aforementioned temperature range and the conversion was found to range from about 3% to about 20%. The screw speed was set to about 300 RPM.

The above detailed description is presented to enable any person skilled in the art to make and use the invention. Specific details have been revealed to provide a comprehensive understanding of the present invention, and are used for explanation of the information provided. These specific details, however, are not required to practice the invention, as is apparent to one skilled in the art. Descriptions of specific applications, analyses, and calculations are meant to serve only as representative examples. Various modifications to the preferred embodiments may be readily apparent to one skilled in the art, and the general principles defined herein may be applicable to other embodiments and applications while still remaining within the scope of the invention. There is no intention for the present invention to be limited to the embodiments shown and the invention is to be accorded the widest possible scope consistent with the principles and features disclosed herein.

While various embodiments of the present invention have been described above, it should be understood that they have been presented by way of example and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above-described exemplary embodiments.

The compositions, processes, systems, and methods of the present invention are often best practiced by empirically determining the appropriate values of the operating parameters, or by conducting simulations to arrive at best design for a given application. Accordingly, all suitable modifications, combinations, and equivalents should be considered as falling within the spirit and scope of the invention.

REFERENCES

Agag, T.; Geiger, S.; Alhassan, S. M.; Qutubuddin, S.; Ishida, H., *Macromolecules* 2010, 43 (17), 7122-7127.
Allen, D. J.; Ishida, H., *Polymer* 2009, 50 (2), 613-626.
Andersen, P. G.; Lechner, F., *Proc. SPE* 2013.
Baranek, A. D. Design and synthesis of flexible and functional polybenzoxazine thin films. Ph. D., The University of Southern Mississippi, Ann Arbor, 2013.
Brunovska, Z.; Liu, J. P.; Ishida. H., *Macromol. Chem. Phys.* 1999, 200 (7), 1745-1752.
Burke, W. J.; Weatherbee, C., *J. Am. Chem. Soc.* 1950, 72 (10), 4691-4694.
Burke, W. J., *J. Am. Chem. Soc.* 1949, 71 (2), 609-612.
Burke, W. J.; Stephens, C. W., *J. Am. Chem. Soc.* 1952, 74 (6), 1518-1520.
Burke. W. J.; Bishop, J. L.; Glennie. E. L. M.; Bauer, W. N., *J. Org. Chem.* 1965, 30 (10), 3423-3427.
Cai, C.; Shi, Q.; Li, L.; Zhu, L.; Yin, J., *Radiat. Phys. and Chem.* 2008, 77 (3), 370-372.
Easton, R. W. British Patent No. 109,663. 1916.
Easton, R. W. U.S. Pat. No. 1,468,379. 1923.
Fang, H.; Ma, X.; Feng, L.; Wang, K.; Cao, B., *J. Appl. Polym. Sci.* 2008, 108 (6), 3652-3661.
Finnigan, B.; Martin, D.; Halley, P.; Truss, R.; Campbell, K., *Polymer* 2004, 45 (7), 2249-2260.
Higginbottom, H. P. Polymerizable compositions comprising polyamines and poly(dihydrobenzoxazines). 1988.
Higginbottom, H. P.; Drumm, M. F. Process for deposition of resin dispersions on metal substrates. 1988.
Holly, F. W.; Cope, A. C., *J. Am. Chem. Soc.* 1944, 66(11), 1875-1879.
Ishida, H. A., T, *Handbook of Benzoxazine Resins*. Elsevier: Amsterdam, 2011; Vol. 1.
Ishida, H., Process for preparation of benzoxazine compounds in solventless systems, U.S. Pat. No. 5,543,516, Aug. 6, 1996.
Kimura, H.; Ohtsuka, K.; Matsumoto, A., Chapter 24—Poly (Benzoxazine/Bisoxazoline). *Handbook of Benzoxazine Resins*, Agag, H. I., Ed. Elsevier: Amsterdam, 2011; pp 429-441.
Moad, G., *Prog. Polym. Sci.* 1999, 24 (1), 81-142.
Ning, X.; Ishida, H., *J. Polym. Sci. Part A: Polym. Chem.* 1994, 32 (6), 1121-1129.
Prat, L.; N'Diaye, S.; Rigal, L.; Gourdon, C., *Chemical Engineering and Processing: Process Intensification* 2004, 43 (7), 881-886.
Rimdusit, S.; Jongvisuttisun, P.; Jubsilp, C.; Tanthapanichakoon, W., *J. Appl. Polym. Sci.* 2009, 111 (3), 1225-1234.
S. B. Brown, C. M. O., Reactive Extrusion. *Encyclopedia of Polymer Science and Engineering*, John Wiley: New York, 1988; Vol. 14, p 169.
Schreiber, H. German Patent 2,255,504. 1973.
Schreiber, H. Polymeric resins derived from 1-oxa-3-aza tetraline group-containing compounds and cycloaliphatic epoxides. 1986.
Shokoohi, S.; Arefazar, A.; Naderi, G., *Mat. Des.* 2011, 32 (3), 1697-1703.
Titier, C.; Pascault, J.-P.; Taha, M., *J. Appl. Polym. Sci.* 1996, 59 (3), 415-423.
Tzoganakis, C., *Adv. Polym Tech.* 1989, 9 (4), 321-330.
Wang, Y.-X.; Ishida, H., *J. Appl. Polym. Sci.* 2002, 86 (12), 2953-2966.
Ward, S.; Harriman, M. Benzoxazines and Compositions Containing the Same. US Patent Application 2013/026759. 2013.
Wunsche, A. German Patent 131,392. 1901.
Xanthos, M., *Reactive extrusion: principles and practice*. Hanser Publishers; Distributed in the USA and Canada by Oxford University Press: Munich; New York N.Y., 1992; p xv, 304 p.
Yeganeh, H., Chapter 21—Polybenzoxazine/Polyurethane Alloys. *Handbook of Benzoxazine Resins*, Agag, H. I., Ed. Elsevier: Amsterdam, 2011; pp 389-403.
Zhang, C.; Wang, L.; Yu, R.; Zheng, S., Chapter 25—Morphology and Properties of Polybenzoxazine Blends. *Handbook of Benzoxazine Resins*, Agag, H. I., Ed. Elsevier: Amsterdam, 2011; pp 445-455.

What is claimed is:

1. A method to melt synthesize a benzoxazine monomer alloy, maleimide monomer alloy, or both, from a known variant of at least one base reactant, the method comprising:
utilizing in a reactor at least one base reactant from a batch of pre-blended reactants for the synthesis, wherein the at least one base reactant is a phenol, amine, paraformaldehyde, or a combination thereof, and
forming the benzoxazine monomer alloy, maleimide monomer alloy, or both, using a continuous, high shear reactor at a processing temperature of from about 90° C. to about 200° C. and a residence time of about 30 to about 60 seconds for benzoxazines and from about 160° C. to about 300° C. and a residence time of about 90 seconds for maleimides,
wherein the benzoxazine monomer alloy is comprised of a monofunctional benzoxazine monomer, a multifunctional benzoxazine monomer, a maleimide monomer, a bismaleimide monomer, or a combination thereof, and wherein the combination is at a ratio of from about 0 weight percent to about 100 weight percent monofunctional to multifunctional heterocyclic monomer and the chemical structure of the benzoxazine monomer is:

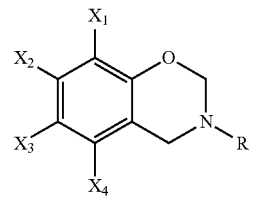

where substituents $X_{1-4}$ on phenol are X groups and can be an electron withdrawing group selected from the group consisting of F, Cl, Br, I, COH, CN, $COCH_3$, $COOCH_3$, $SO_3H$, and $NO_2$, or an electron donating group selected from the group consisting of $OCH_3$ or $CH_3$, hydrogen (H), alkyl ($C_{1-8}$ alkyl), cycloalkyl ($C_{5-7}$ cycloalkyl), and aryl, and where the aryl and the cycloalkyl can also include or contain substituents such as and from the electron withdrawing group or the electron donating group, or both, and the R is at least one group on a primary amine and can be selected from the group consisting of H, $C_{1-8}$ alkyl, $C_{5-7}$ cycloalkyl, and aryl, and the aryl and the cycloalkyl can be substituted with or contain any of the X groups, R groups, or both, and the chemical structure of the maleimide monomer is:

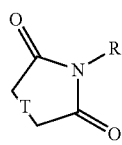

where T on the anhydride structure can be a double bond, a single bond, or can contain additionally bonded substituents at either carbon of T, an electron donating group selected from the group consisting of $OCH_3$ or $CH_3$, hydrogen (H), alkyl ($C_{1-8}$ alkyl), cycloalkyl ($C_{5-7}$ cycloalkyl), and aryl, and where the aryl and the cycloalkyl can be substituted with or contain any substituents such as and from the electron donating group, and the R is at least one group on a primary amine and can be selected from the group consisting of H, $C_{1-8}$ alkyl, $C_{5-7}$ cycloalkyl, and aryl.

2. The method of claim 1, wherein the monofunctional benzoxazine monomer, multifunctional benzoxazine monomer, or both, is a room temperature liquid.

3. The method of claim 2, wherein the monofunctional benzoxazine monomer and the multifunctional benzoxazine monomer are fed to the reactor independently from each other.

4. The method of claim 2, wherein the monofunctional benzoxazine monomer and the multifunctional benzoxazine monomer are fed to the reactor from a blended batch.

5. The method of claim 1, wherein the monofunctional benzoxazine monomer, multifunctional benzoxazine monomer, or both, is a room temperature solid.

6. The method of claim 5, wherein the monofunctional benzoxazine monomer and the multifunctional benzoxazine monomer are fed to the reactor independently from each other.

7. The method of claim 5, wherein the monofunctional benzoxazine monomer and the multifunctional benzoxazine monomer are fed to the reactor from a blended batch.

8. A method to melt synthesize a benzoxazine prepolymer alloy final product, from a known variant of at least one base reactant, the method comprising:
utilizing in a reactor at least one base reactant from a batch of pre-blended reactants for the synthesis, wherein the at least one base reactant is a phenol, amine, paraformaldehyde, or a combination thereof, and
forming the benzoxazine prepolymer alloy using a continuous, high shear reactor at a processing temperature of from about 90° C. to about 200° C. and a residence time of about 60 to about 90 seconds,
wherein the benzoxazine prepolymer alloy is comprised of a monofunctional benzoxazine monomer, a multifunctional benzoxazine monomer, or a combination thereof, and wherein the combination is at a ratio of from about 0 weight percent to about 100 weight percent monofunctional to multifunctional heterocyclic monomer.

9. The method of claim 8, wherein the monofunctional benzoxazine monomer, multifunctional benzoxazine monomer, or both, is a room temperature liquid.

10. The method of claim 9, wherein the monofunctional benzoxazine monomer and the multifunctional benzoxazine monomer are fed to the reactor independently from each other.

11. The method of claim 9, wherein the monofunctional benzoxazine monomer and the multifunctional benzoxazine monomer are fed to the reactor from a blended batch.

12. The method of claim 8, wherein the monofunctional benzoxazine monomer, multifunctional benzoxazine monomer, or both, is a room temperature solid.

13. The method of claim 12, wherein the monofunctional benzoxazine monomer and the multifunctional benzoxazine monomer are fed to the reactor independently from each other.

14. The method of claim 12, wherein the monofunctional benzoxazine monomer and the multifunctional benzoxazine monomer are fed to the reactor from a blended batch.

15. The method according to any of claims 1 through 14, further comprising adding to the synthesis a reactive diluent at a weight ratio of up to about 100 weight percent, wherein the reactive diluent is a monofunctional or multifunctional epoxy, a monofunctional or multifunctional curative, or a combination thereof, and optionally adding to the synthesis at least one reinforcement from the group consisting of carbon nanotubes, graphene, POSS, silica, carbon black, and fibers, at least one additive from the group consisting of pigments, organic matter, dispersants, molecular sieves, and flocculants, or a combination of at least one reinforcement and at least one additive thereof, wherein the addition of any reinforcement or additive is at a weighted ratio of from about 0 to about 100 weight percent and the synthesis is in-solvent or is solvent-free for reducing isomer formation and for producing predictable prepolymer conversion.

* * * * *